(12) United States Patent
Shannon et al.

(10) Patent No.: US 8,992,829 B2
(45) Date of Patent: *Mar. 31, 2015

(54) SPORTS EQUIPMENT AND FACILITY DISINFECTION

(75) Inventors: Michael Edward Shannon, Picton (CA); Dick Eric Zoutman, Kingston (CA)

(73) Assignee: Medizone International Inc., Stinson Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/821,492

(22) PCT Filed: Sep. 7, 2011

(86) PCT No.: PCT/CA2011/510542
§ 371 (c)(1),
(2), (4) Date: Mar. 7, 2013

(87) PCT Pub. No.: WO2012/031364
PCT Pub. Date: Mar. 15, 2012

(65) Prior Publication Data
US 2013/0164172 A1    Jun. 27, 2013

Related U.S. Application Data

(60) Provisional application No. 61/380,825, filed on Sep. 8, 2010.

(51) Int. Cl.
*A61L 2/20*    (2006.01)

(52) U.S. Cl.
CPC ............... *A61L 2/202* (2013.01); *A61L 2/208* (2013.01); *A61L 2202/26* (2013.01)
USPC .......................................................... 422/28

(58) Field of Classification Search
CPC ............ A61L 2/20; A61L 2/202; A61L 2/208
USPC .......................................................... 422/28
See application file for complete search history.

(56) References Cited

U.S. PATENT DOCUMENTS

| 5,316,741 | A |   | 5/1994 | Sewell et al. |
| 5,666,640 | A | * | 9/1997 | Daniylchev ............... 422/186.1 |

(Continued)

FOREIGN PATENT DOCUMENTS

| CA | 2473540 A1 | 7/2003 |
| CA | 2486831 | 2/2004 |

(Continued)

OTHER PUBLICATIONS

US Environmental Protection Agency Office of Pesticide Programs List H: EPA's Registered Products Effective Against MRSA and VRE. Jan. 9, 2009.*

(Continued)

*Primary Examiner* — Sean E Conley
*Assistant Examiner* — Donald Spamer
(74) *Attorney, Agent, or Firm* — Durham Jones & Pinegar, P.C. Intellectual Property Law Group (57) ABSTRACT

A process for treating sports equipment and sports facility rooms to inactivate "superbug" bacteria such as MRSA, VRE and *P. aeroginosa*, which comprises subjecting the equipment or the room, and surfaces therein, to a disinfecting atmosphere which includes ozone at a concentration of 2-350 ppm by weight and hydrogen peroxide at an amount of 0.2-10 wt. %, at a relative humidity of at least 60%, and for a period of at least 30 minutes sufficient for an effective kill of the bacteria; and subsequently removing ozone from the atmosphere, down to 0.04 ppm or less.

20 Claims, 5 Drawing Sheets

(56) References Cited

U.S. PATENT DOCUMENTS

| | | | |
|---|---|---|---|
| 6,045,846 | A | 4/2000 | Bautista et al. |
| 7,217,685 | B2 | 5/2007 | McDonnell et al. |
| 7,393,818 | B2 | 7/2008 | McDonnell et al. |
| 7,407,624 | B2 | 8/2008 | Cumberland et al. |
| 8,551,399 | B2 * | 10/2013 | Shannon et al. ............ 422/28 |
| 8,636,951 | B2 * | 1/2014 | Shannon et al. ............ 422/28 |
| 2003/0039729 | A1 | 2/2003 | Murphy et al. |
| 2003/0132279 | A1 | 7/2003 | Stemmle |
| 2005/0129571 | A1 | 6/2005 | Centanni |
| 2005/0226764 | A1 | 10/2005 | Moirandat et al. |
| 2006/0104858 | A1 | 5/2006 | Potember et al. |
| 2007/0079455 | A1 | 4/2007 | Brewer et al. |
| 2007/0086914 | A1 * | 4/2007 | Antinozzi ............... 422/28 |
| 2008/0031770 | A1 | 2/2008 | Heselton et al. |
| 2009/0263499 | A1 | 10/2009 | Platt, Jr. et al. |

FOREIGN PATENT DOCUMENTS

| | | |
|---|---|---|
| CA | 2491781 A1 | 7/2005 |
| CA | 2547589 | 7/2005 |
| CA | 2526367 A1 | 4/2007 |
| WO | 2004011041 | 2/2004 |
| WO | 2005060385 | 7/2005 |
| WO | 2009046562 | 4/2009 |
| WO | 2011003179 | 1/2011 |
| WO | 2011085466 | 7/2011 |

OTHER PUBLICATIONS

Canadian Intellectual Property Office, "International Search Report and Written Opinion," issued in International Patent Application No. PCT/CA20111050544, dated Dec. 28, 2011.

Canadian Intellectual Property Office, "International Search Report and Written Opinion," issued in International Patent Application No. PCT/CA2011/050543, dated Dec. 19, 2011.

Canadian Intellectual Property Office, "International Search Report and Written Opinion," issued in International Patent Application No. PCT/CA2011/050542, dated Dec. 9, 2011.

United States Patent and Trademark Office, "Office Action," issued in U.S. Appl. No. 13/343,403, dated Oct. 25, 2012.

Canadian Intellectual Property Office, "International Search Report and Written Opinion," issued in International Patent Application No. PCT/CA2010/000998, dated Oct. 7, 2010.

Canadian Intellectual Property Office, "International Preliminary Report on Patentability," for International Patent Application No. PCT/CA2010/000998, dated Jul. 27, 2011.

"Prospects for Managed Underground Storage of Recoverable Water," National Research Council, 2008, p. 243.

"Ozone effects on bacteria, molds and viruses—ozone and bacteria destruction" published Dec. 24, 2007, http://web.archive.org/web20071224191320/http://www.ozoneapplications.com/info/ozone_bacteria_mold_viruses.htm.

Richard P. Wenzel, et al., "The Impact of Hospital-Acquired Bloodstream Infections", Emerging Infectious Diseases, vol. 7, No. 2, Mar.-Apr. 2001, pp. 174-177.

Dr. Carsten Matz, et al., "Biofilm Bacteria Protect Themselves with Chemical Weapons", Helmholtz Centre for Infection Research, Bauschweig, reported on Informiac.com, Jul. 23, 2008.

United States Patent and Trademark Office, "Office Action," issued in U.S. Appl. No. 13/343,403, dated Mar. 25, 2013.

"Amendment after Non-Final Rejection and Notice of Non-Compliant Amendment," filed Feb. 25, 2013 in U.S. Appl. No. 13/343,403 in response to Notice of Non-Compliant Amendment of Feb. 20, 2013, and Non-Final Office Action of Oct. 25, 2012.

"Amendment Under 37 C.F.R. §1.116 With Request for Consideration Under the Final Consideration Pilot Program 2.0," filed Jun. 25, 2013 in U.S. Appl. No. 13/343,403 in response to final Office Action of Mar. 25, 2013.

"Supplemental Amendment," filed Jul. 19, 2013 in U.S. Appl. No. 13/343,403 in response to final Office Action of Mar. 25, 2013 and the telephonic interview with the Examiner of Jul. 19, 2013.

United States Patent and Trademark Office, "Comments on Statement of Reasons for Allowance," filed Sep. 6, 2013 in U.S. Appl. No. 13/343,403 in response to Notice of Allowability dated Aug. 2, 2013.

World Intellectual Property Organization "Amendment Pursuant to Art. 19 of the Patent Cooperation Treaty" for PCT Application No. PCT/CA2010/000998, Dec. 2, 2010, 14 pages, Ottawa, Ontario, Canada.

Canada Intellectual Property Office "Amendment Under Art. 34" issued in to PCT Application No. PCT/CA2010/000998, Mar. 1, 2011, 7 pages, Ottawa, Ontario, Canada.

United States Patent and Trademark Office, "Notice of Allowability" issued in U.S. Appl. No. 13/343,403 dated Aug. 2, 2013.

Canadian Intellectual Property Office, "International Search Report and Written Opinion, " issued in International Patent Application No. PCT/CA2010/001364, dated Dec. 3, 2010.

Patent Cooperation Treaty, "Notification of the Recording of a Change" issued in PCT Application No. PCT/CA12010/000998 dated Mar. 17, 20111.

Rogers et al., "*Bacillus anthracis* Spore Inactivation by Fumigant Decontamination", Applied Biosaftey, 2008, vol. 13, No. 2, pp. 89-98, available at http://www.absa.org/abj/abj/081302Rogers.pdf.

Whitney et al., "Inactivation of *Bacillus anthracis* Spores", Emerging Infectious Diseases, Jun. 2003, vol. 9, No. 6, pp. 623-627, available at http://wwwnc.cdc.gov/eid/article/9/6/pdfs/02-0377.pdf.

\* cited by examiner

SPORTS EQUIPMENT AND FACILITY DISINFECTION

CROSS-REFERENCE TO RELATED APPLICATIONS

This application is the national stage under 35 U.S.C. §371 of International Patent Application No. PCT/CA2011/050542, filed Sep. 7, 2011, designating the United States, and published Mar. 15, 2012 as International Publication No. WO/2012/031364, which application claims priority to and the benefit of U.S. patent application Ser. No. 61/380,825 filed on Sep. 8, 2010. The disclosures of the above-identified applications are expressly incorporated herein by this reference in their entireties.

FIELD OF THE INVENTION

This invention relates to sports equipment and sports facility disinfection treatments. More particularly, it relates to processes and systems for disinfecting sports apparel such as athletes' clothing and protective equipment, and sports premises such as locker rooms, change rooms and gymnasiums, of bacteria such as the highly infectious, potentially lethal *Methicillin Resistant Staphylococcus Aureus* (MRSA), *Psuedomonas aeroginosa, E. Coli* and vancomycin-resistant *enterrococcus* (VRE).

BACKGROUND OF THE INVENTION

MRSA, *P. aeroginosa, E. coli* and VRE are regarded as a "superbugs," antibiotic-resistant bacteria responsible for serious infections in hospitals and other healthcare facilities ("nocosomial" infections). Such infections are approaching epidemic proportions. These bacteria are resistant to standard cleaning procedures and most antibiotics.

Compounding the difficulties in combating MRSA and other superbug growth and infections is the fact that the organisms grows within biofilms which form on surfaces and which protect the bacteria from adverse environmental factors. A biofilm is an aggregate of microorganisms in which the cells adhere to each other and/or to a surface. They are frequently embedded in a self-produced matrix of extracellular polymeric substance (EPS), a polymeric conglomeration generally composed of extracellular DNA, proteins and polysaccharides. Biofilms form on surfaces, including fabric, fibrous and porous surfaces, such as wearing apparel, liners, drapes, carpets and fibrous contents of walls, screens, ceilings and room dividers.

As reported in a recent article entitled "Assessment of Athletic Facility Surfaces for MRSA in the Secondary School Setting" (Journal of Environmental Health, Feb., 2010), the authors stated that "*Methicillin-Resistant Staphylococcus Aureus* (MRSA) was once largely a hospital-acquired infection, but increasingly, community-associated MRSA (CA-MRSA) is causing outbreaks among otherwise healthy people in athletic settings. Secondary school athletic trainers, student athletes, and the general student population may be at elevated risk of MRSA infection."

BRIEF REFERENCE TO THE PRIOR ART

Sanitation of sports clothing and equipment is attempted through laundering and disinfectant topical application, but is not wholly effective where MRSA is concerned. Chlorinated solutions with and without ammonia are commonly used to clean and disinfect athletic facility rooms such as change rooms and gymnasia, but have only limited effectiveness against superbugs such as MRSA. Vaporized hydrogen peroxide (VHP) is highly effective when applied to smooth surfaces, but is ineffective on porous materials and fabrics. Ozone is known to be a powerful anti-fungal and anti-viral agent, and has been used in water purification for many years. However, use of ozone in a gaseous atmosphere for anti-bacterial purposes is problematic, because of its harmful medical effects (irritation of eyes and mucous membranes, pulmonary edema and chronic respiratory disease). Moreover, ozone poses an environmental hazard.

Once a porous, soft surface such as carpet, drapery, porous material in ceilings and the like becomes impregnated with bacteria, it cannot be effectively disinfected using currently available agents and processes.

Canadian Patent application 2,526,367 Scullion et.al. published Apr. 19, 2007, proposes the use of ozone to clean and disinfect sports equipment. The system includes a high velocity internal distribution system that penetrates the system with ozone.

U.S. Pat. No. 7,407,624 Cumberland et.al., issued Aug. 5, 2008, describes methods for abating pathogens in air, using an atmosphere having specific combinations of ozone concentration, hydrogen peroxide concentration, temperature and humidity. Locker rooms are mentioned, among the very wide range of possible targets. The patent does not mention combating superbugs, and does not mention application to surfaces. Its single working example is non-specific about the conditions used.

It is an object of the present invention to provide a novel and effective method of treating sports facilities, sports equipment and sports objects infected or prone to infection with MRSA bacteria and other superbugs.

SUMMARY OF THE INVENTION

The present invention provides, from one aspect, a process for treating sports equipment and sports facility rooms to inactivate "superbug" bacteria such as MRSA, VRE and *P. aeroginosa*, which comprises subjecting the equipment or the room, and surfaces therein, to a disinfecting atmosphere which includes ozone at a concentration of 2-350 ppm by weight and hydrogen peroxide at an amount of 0.2-10 wt. %, at a relative humidity of at least 60%, and for a period of at least 30 minutes sufficient for an effective kill of the bacteria, and subsequently removing ozone from the atmosphere, down to 0.04 ppm or less.

According to another aspect, there is provided a portable system for disinfecting sports facility rooms such as locker rooms and gymnasiums, and sports equipment contained therein, comprising an ozone generator for discharging into the room a gaseous mixture including ozone; an ozone controller adapted to control the amount of discharged ozone; a source of hydrogen peroxide for discharging controlled amounts of hydrogen peroxide into the room; means for discharging the hydrogen peroxide and ozone into the room; humidity adjusting means adapted to increase or decrease the relative humidity of the room during treatment; and an ozone remover adapted to destroy ozone, down to a safe level in the room atmosphere for subsequent human utilization.

BRIEF REFERENCE TO THE DRAWINGS

THE PREFERRED EMBODIMENTS

Preferred ozone amounts for use in the invention are from about 20-350 parts per million in the disinfection atmosphere, more preferably 20-200 parts per million. Preferred amounts of hydrogen peroxide are the amounts supplied to the disinfecting atmosphere using an aqueous solution containing 0.2-10%, more preferably 1-5%, hydrogen peroxide. In the description below, the peroxide percentages used are sometimes expressed in terms of these solution percentages. The amounts are chosen so that no serious deleterious effects are suffered by other equipment in the sports facility or components of the sports equipment which the disinfecting atmosphere is supplied. The amount of hydrogen peroxide in the disinfecting atmosphere can be calculated from the volume of aqueous hydrogen peroxide evaporated into the disinfecting atmosphere, the volume of the room being disinfected and the concentration of hydrogen peroxide in the starting solution. Times of exposure of the sports facility room (locker room, gymnasium, etc.) and its surfaces, and the sports equipment items, to the disinfecting atmosphere are suitably from 30 minutes to about 120 minutes, preferably from about 60 to about 105 minutes, and most preferably about 90 minutes. These times are constrained to some extent by the need to clear a room of ozone (down to a maximum of 0.04 ppm) following the disinfection phase, and return the room to normal use within a reasonable period of time, with the entire start-to-finish time not exceeding 150 minutes. The ozone removal is an extremely rapid and fully effective process. Both the hydrogen peroxide and the ozone (and any products of interaction between them) should be removed before the room is put back into normal use.

The preferred portable system for destroying superbugs such as MRSA according to the present invention includes, as part of its means for discharging the hydrogen peroxide and ozone into the room, a dislodgement system at the outlet end of the discharging means. The dislodgement system allows penetration of carpet, drapes and similar porous surfaces in the room, and fabric and other porous surfaces on the sports equipment item, to gain access to concealed/sequestered colonies of MRSA bacteria, and to attack MRSA bacteria protected by a biofilm formed on surfaces in the room or on the equipment and embedding the bacteria and spores therein. The dislodgement system can be manually operated, with operators protected by a hazard suit and mask, or remotely operated or totally automated. It may take the form of one or more outlet jets, with associated manually operable jet pressure controls. It may take the form of a revolving or fixed brush with bristles of appropriate stiffness, alone or in combination with an outlet jet. Any form of dislodgement system effective to disturb the pile of carpet fabrics, upholstery fabrics and the like so as to access the remote parts which might harbor MRSA colonies can be used. This includes non-physical applications such as air jets, ultrasonic energy, radio-frequency energy and electromagnetic waves, for example, capable of causing physical disruption and which result in micro-physical movements of fibrous surfaces.

The ozone for use in the present invention can be generated by any known means. In the case of corona or other electrical discharge generation from oxygen, the apparatus of the invention preferably includes a container of medical grade oxygen. The oxygen container can be a standard, pressurized vessel containing medical grade oxygen, of the type commonly found in medical facilities. Oxygen from this container is fed to an ozone generator, where the oxygen is subjected to electrical discharge, normally with a high voltage alternating current, to convert small amounts of the oxygen to ozone and produce a gaseous mixture of oxygen and ozone. The quantity of ozone in the mixture is controllable by adjustment of the voltage of the electrical discharge. Suitable ozone generators are known and available commercially. The relative amounts of ozone generated are relatively small, expressed in parts per million (ppm), but such is the power of ozone as a disinfectant, especially in combination with hydrogen peroxide in accordance with this invention, that such small quantities are all that is required.

Alternative forms of ozone generation can be used if preferred. Ultraviolet radiation of appropriate wavelength, incident upon oxygen or air, is one acceptable alternative. In such a system, air from the room itself may be fed into the ozone generating unit to supply the required oxygen for conversion to ozone. Other methods of ozone generation which can be used include photocatalytic reactions, cold plasma, etc.

The relative humidity of the disinfecting atmosphere in the treatment space should be at least 60% and preferably at least 65%, for effective disinfection. To ensure this, one can incorporate a humidifier in the system of the invention, using sterile water from an internal system reservoir to adjust and control the humidity of the issuing gas mixture. In this way, desirable humidity for the most effective disinfection is achieved at the point of discharge where dislodgement of a carpet or drapery surface can take place. Since the adjustable humidifier need only increase the humidity of the space to the desirable level, however, it can be placed in any location within the space. In one embodiment, the hydrogen peroxide vapor is applied, in controlled amounts, to the air/water vapor issuing from the humidifier and thus is added to the ozone/oxygen containing gas mixture. Alternatively, hydrogen peroxide can be applied to the water used to humidify the target location. Hydrogen peroxide is commercially available as aqueous solutions of standard concentrations of hydrogen peroxide. For use in embodiments of the present invention, a standard solution of known peroxide concentration is suitably diluted down by a fixed volume of distilled water. The peroxide load is standardized based on the known volume of water from the peroxide solution required to raise the relative humidity to the desired extent, e.g. from 40-80%. From this, the amount of hydrogen peroxide in volume % or ppm by volume introduced into the treatment facility can be calculated.

Certain systems according to embodiments of the invention may include a temperature adjuster and controller for the gas mixture. This can be a simple heater/cooler through which either the incident oxygen or the generated oxygen/ozone mixture passes prior to discharge into the room's atmosphere. While simple adjustment of the temperature of the room using an external room heating system and thermostat can be effective, it is preferred to adjust the temperature of the issuing gas mixture, for most effective treatment of the carpet and drapery surfaces. The ideal range of temperature for ozone and ozone/hydrogen peroxide decontamination of MRSA, VRE and *P. aeroginosa* is 15-30° C.

The system of the invention also preferably includes an ozone removal unit. Such units are known, and can be purchased commercially for use in the present invention. Depending on the volume of the room atmosphere and the capacity of the ozone removal unit, more than one such unit may be incorporated in the system of the invention. Suitable ozone removal units are those based on activated carbon as the removal medium. These act very quickly, and do not lead to the formation of hazardous reaction products. The inclusion of such units enables the treated facility to be cleared of ozone and returned to normal use rapidly, for economic reasons. Other types include systems based on catalysts such as manganese oxide or other metal oxides, which may be heated to remove moisture, or thermal destruction in conjunction with other metals including platinum or palladium.

Figure 1:
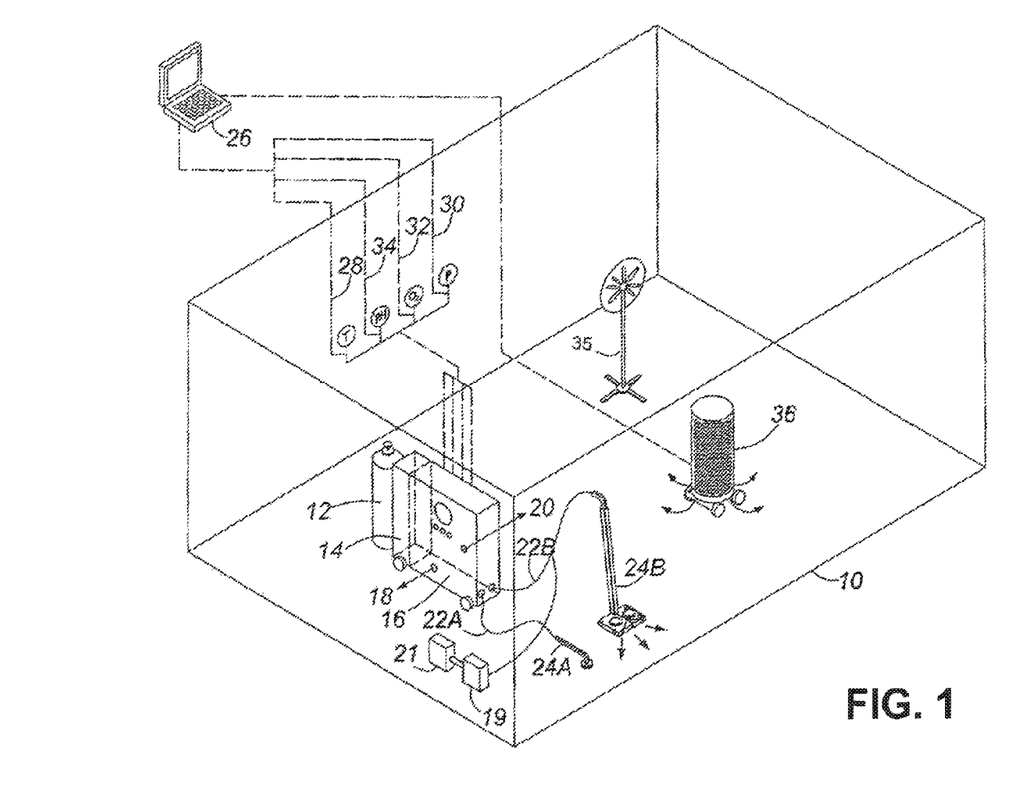
FIG. 1 of the accompanying drawings is a diagrammatic illustration of an apparatus in accordance with an embodiment of the invention, disposed within a sports facility room to be disinfected.

FIG. 1 of the accompanying drawings shows a room 10 such as a locker room, liable to superbug (e.g., MRSA, etc.) bacterial contamination and closed, ready for disinfection by a process according to an embodiment of the invention. The room is substantially sealed, to minimize escape of ozone. Inside the room is a pressurized cylinder 12 of oxygen, feeding oxygen gas into a humidifier 14 and thence to an ozone generator 16, which includes electrical discharge plates of variable voltage to adjust the quantity of ozone which is generated. A heater and a pressure controller (not shown) may be disposed near the entrance to the ozone generator 16. The oxygen/ozone gas mixture is output via room outlets 18, 20 to the atmosphere of the room 10, and via wands 22A and/or 22B to a dislodgement means 24A and 24B in the form of respective scrubbing brushes mounted on the outlet ends of the respective wands 22A, 22B. The heater, the pressure controller, the voltage supplied to the ozone generator 16 and the humidity level supplied by the humidifier 14 are all controlled and adjusted from an external control panel 26 via respective electrical connections 28, 30, 32 and 34. Also disposed within the room is an oscillating fan 35 and an ozone destruct filter unit 36.

Disposed within the room 10 is a container of aqueous hydrogen peroxide solution 19 and associated air blower 21 which, during operation, blows vaporized hydrogen peroxide in controlled amounts into discharge wand 22A and 22B to mix with the output of ozone/oxygen therein. The amount of hydrogen peroxide being supplied is controlled by adjustment of the blower 21 through a connection to the control panel 26. In an alternative arrangement, hydrogen peroxide can be supplied from generator 19 to the humidifier 14.

Figure 2A:
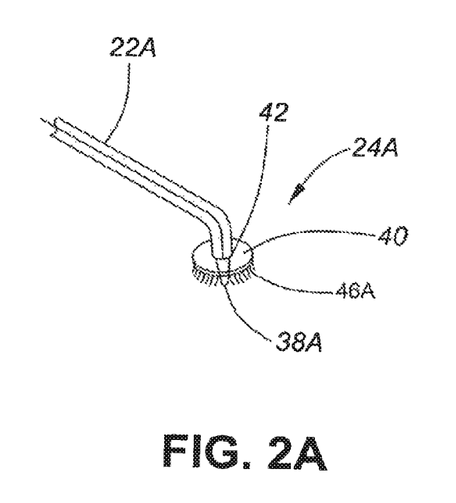
FIGS. 2A and 2B are diagrammatic illustrations of physical agitation systems for use in embodiments of the invention.
Figure 2B:
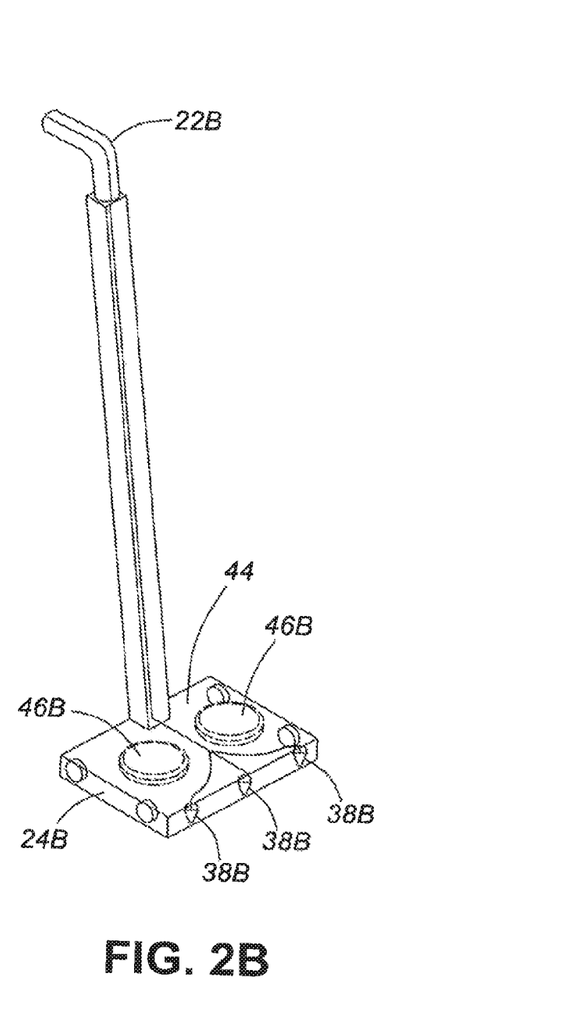

FIGS. 2A and 2B of the accompanying drawings show in more detail forms of dislodgement means 24A and 24B for use in the present invention, attached to the outlet, discharge ends of respective wands 22A and 22B. The dislodgement means 24A has a jet outlet nozzle 38A at its extremity, and a generally circular plate 40 mounted on the wand 22A near the discharge end. The wand 22A passes through a central aperture 42 in a plate 40. The plate 40 has brush bristles 46A mounted on its lower surface, arranged in two arcs around the jet outlet nozzle 38A and protruding downwardly to an extent just beyond the extent of outlet from nozzle 38A. In use, an oxygen/ozone gas mixture or oxygen/ozone/hydrogen peroxide gas mixture issues from nozzle 38A at a relatively high pressure, and can be directed by the operator holding the wand 22A to a carpet surface area, fibrous-surfaced upholstery area, drapery, etc, while at the same time the operator scrubs the surface area with the bristles 46A.

FIG. 2B shows an alternative but essentially similar arrangement, in which plate 40 is replaced by a wheeled platform 44 carrying two rotary brushes 46B and three gas jet outlets 38B for the oxygen/ozone/hydrogen peroxide delivery at pressure, located forwardly of the rotary brushes 46B.

Figure 3:
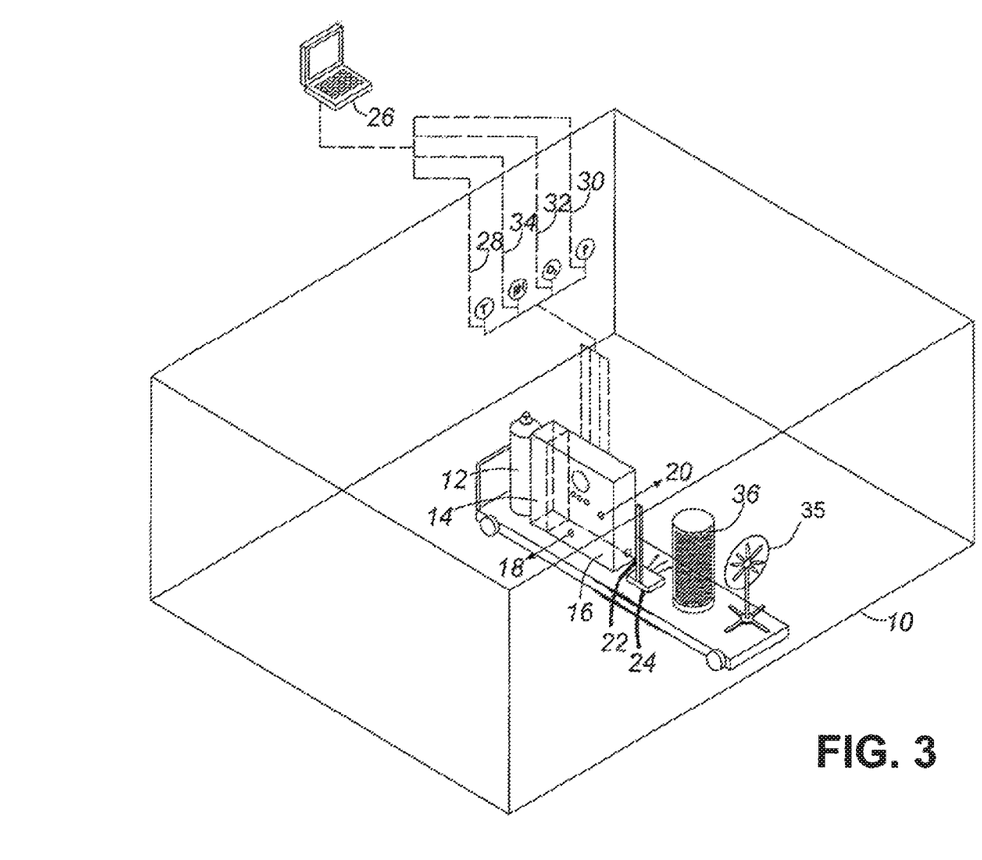
FIG. 3 is a diagrammatic illustration of an apparatus according to the invention, in a portable, transportation mode.

FIG. 3 of the accompanying drawings illustrates the portability of a system according to the invention. Parts are numbered as in FIG. 1. A 4-wheeled cart 48 is provided, on which all the component parts of the system can be loaded for ease of transportation from one room to another. The instrumentation and control panel can be disconnected for transportation, and re-connected and disposed outside when the apparatus is placed in another room for use as shown in FIG. 1. The cart 48 is removed while the system is in use, but is loaded with the components after use, either for transportation to another room or for storage.

The operation of the system will be readily apparent from the preceding description of its component parts and their inter-connection. The cart 48 carrying the component parts is wheeled into the room 10 to be disinfected, and the parts are distributed around the room and connected together as illustrated in FIG. 1. An operator wearing a hazard suit and other appropriate protective clothing enters the room and holds the wand 22. The room 10 is sealed. Conditions of treatment are set on the control panel 26, and the apparatus is switched on so that the oxygen/ozone/hydrogen peroxide gas mixture at controlled ozone concentration, hydrogen peroxide concentration, relative humidity, temperature and elevated pressure issues from jet nozzle 38. The operator applies the jetted gas mixture to the carpet surfaces, drapery surfaces and other absorbent surfaces in the room 10, and to the fibrous and porous surfaces of sports equipment in the room 10, scrubbing the surfaces at the same time with the dislodgement means 24. The room 10 may become pressurized above atmospheric pressure, due to the introduction of the oxygen/ozone gas mixture. Pressure is continually monitored by the control panel 26 to ensure safe working conditions for the operator, as well as the temperature, humidity and ozone concentration in the room 10. Smooth surfaces in the room may not need the action of the dislodgement means 24, but are satisfactorily disinfected by contact with the disinfecting atmosphere in the room 10. The oscillating fan 35 is operated throughout the procedure, to circulate the oxygen/ozone mixture throughout the room.

After a pre-set time of the procedure, and after all the appropriate, absorbent surfaces have been scrubbed, a time not normally exceeding 90 minutes, the hydrogen peroxide supply, the oxygen supply and ozone generator are switched off. Then the ozone destruct filter unit 36 is operated, sucking in the ozone-containing gases, destroying the ozone and issuing pure oxygen from it. The room 10 can now be opened, the apparatus disconnected and loaded on the cart 48, and the room 10 put back to its normal use.

The range of sports equipment which can be treated according to the invention is wide and varied. It includes substantially any item of sports equipment which is likely to become contaminated with bacteria as a result of repeated contact with human perspiration. This includes items of clothing such as uniforms, sweaters, jerseys, caps, shorts, pants sweatbands and underwear. It includes footwear such as athletic boots and shoes, skates and trainers. It includes protective items such as helmets, pads and gloves. It also includes non-worn items such as bats, balls, racquets, nets and towels. While such items can be treated according to the invention by suspending them or otherwise placing them in a sports facility room and treating the whole room with the disinfecting atmosphere, it is more effective to give each piece of equipment individual attention, and apply the disinfecting atmosphere to it with physical agitation such as an air jet.

When treating fibrous and porous materials such as textiles, clothing, uniforms, underwear, soft pads, soft upholstery, carpets, drapes and the like, physical agitation to disturb the fibrous surface as the disinfecting atmosphere is applied is particularly beneficial. Pressure jet application from the wand as illustrated, with or without the use of brushes, is effective. As the following specific examples show, much more efficient disinfection is achieved when this physical agitation process is used.

The process of the invention is further described with reference to specific experimental examples.

EXAMPLE 1

Control Swab

A swab was taken from the interior surface of an ice hockey goaltender's glove (blocker), which had been used by a 12-year old boy for three years. The swab was cultivated and tested, and the glove interior was found to be heavily contaminated with MRSA along with other, less deadly pathogens.

More specifically, a single pure colony of MRSA from the swab was inoculated to a Columbia agar plate with 5% sheep's blood. It was incubated at 35° C. in room air for 18-24 hours. From the plate, 4-5 isolated colonies were selected, and suspended in tryptic soy broth to achieve a 0.5 McFarland turbidity standard ($1.5 \times 10^8$ cfu/ml) measured using a spectrophotometer. Inoculum was prepared by performing serial dilutions of 0.9 ml 0.85 NaCl broth with 0.1 ml of original 0.5 McFarland inoculum (4×10 fold) to give solutions of $10^{-1}$, $10^{-2}$, $10^{-3}$, and $10^{-4}$ cfu/mL. Incubation of these serially diluted solutions and subsequent counting of the resulting viable colonies determines the dilution at which growth is eliminated, to be expressed as a log kill. Thus, if growth is eliminated at a three-fold dilution ($10^{-3}$ cfu/ml solution), this is a log 3 kill. This is standard procedure.

The diluted solutions of organisms were plated out, 0.1 ml of each solution being spread over the surface of Columbia sheep's blood agar plates, and the plates placed in an incubator for 24 hours. The surfaces of the agar plates were eluted to remove bacterial colonies, and the eluates plated out for examination and counting of active, reproducing colonies, under a microscope.

The reproducing colonies at $10^{-1}$ and $10^{-2}$ dilutions were too numerous to count. At $10^{-3}$ and $10^{-4}$ dilutions, 312 and 28 reproducing colonies respectively were counted. This indicates the heavy contamination of the glove interior with MRSA after extended use.

EXAMPLE 2

MRSA Control

A single pure colony of MRSA strain ATCC 33592 was inoculated and incubated as described in Example 1. Similar serial dilution of inoculums from 4-5 isolated colonies was conducted, followed by similar incubation and counting of reproducing colonies.

In this case, the reproducing colonies at $10^{-1}$ were too numerous to count. At dilutions $10^{-2}$, $10^{-3}$ and $10^{-4}$, the counts were 219, 39 and 4 respectively. This control experiment in comparison with Example 1 indicates that the wild strains of MRSA from athletic equipment are, if anything, more virulent than the standard, pure MRSA strain ATCC 33592.

EXAMPLE 3

The same ice hockey goaltender's glove as used in Example 1 was treated with ozone and hydrogen peroxide according to the invention, and then swabbed and tested for active reproducing MRSA as described.

Figure 4:
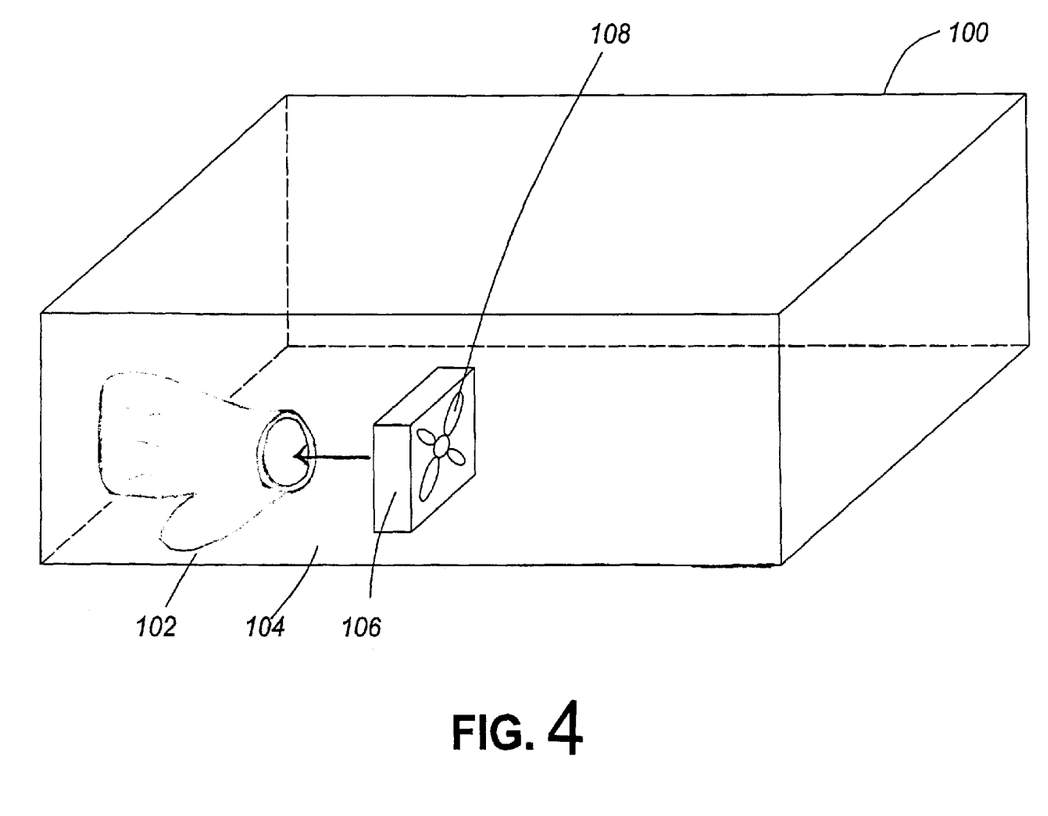
FIG. 4 is a diagrammatic illustration of an apparatus used to disinfect a piece of sports equipment, namely, an ice hockey goal tender's glove, according to the invention, as described in Example 3 below.

An apparatus as diagrammatically illustrated in FIG. 4 was used. A chamber 100, closed while the experiment was in progress, contained near one end the hockey glove 102, supported in the chamber 100 with its open end 104 directed towards and disposed 2 feet from an electrical fan 106 with rotary blades 108. The chamber 100 was filled with a disinfecting atmosphere containing 180 ppm ozone and 3% hydrogen peroxide. The fan 106 blew the atmosphere weakly into the interior of the glove through opening 104. This was continued for 90 minutes. Then the chamber 100 was cleared of disinfecting atmosphere, the glove 102 removed, and a swab taken from its interior, inoculated, cultured and serially diluted as described in Example 1 above.

No viable colonies of MRSA were detected at any of the $10^{-1}$, $10^{-2}$, $10^{-3}$ or $10^{-4}$ dilutions tested.

In a subsequent experiment, the same glove after ozone/hydrogen peroxide exposure to sterilize it effectively as described, was artificially infected with MRSA strain ATCC 33592, which was allowed to incubate on the inside surface of the glove. Then the glove 102 was subjected to the same ozone/hydrogen peroxide treatment in the chamber 100, for the same period of time and under the same conditions as described above. Then the glove interior was swabbed, the swab inoculated, cultured and serially diluted as described above and in Example 1.

No viable MRSA colonies were detected, at any of the same serial dilutions.

EXAMPLE 4

Another series of experiments was conducted, with the same strain of MRSA but deposited onto fibrous carpet of the type found in gymnasia and locker rooms. The MRSA-carrying carpet samples were suspended in a room as generally depicted in accompanying FIG. 1, and the ozone/hydrogen peroxide/water disinfecting atmosphere was blown at the carpet surface with a fan directed towards the carpet, of velocity sufficient to cause physical agitation of the fibrous carpet surface. The agar plates for testing were prepared as previously described in Example 1. Serial dilutions of 10-fold, 100-fold, 1000-fold and 10,000 fold were effected, and the plates incubated. Use of a disinfecting atmosphere of 80 ppm ozone, 1% hydrogen peroxide and 80% relative humidity, for times of 30 minutes in one experiment and 60 minutes in another experiment, produced plates showing no viable colonies of MRSA, at any of the dilutions.

Repeats of these experiments using carpet samples carrying VRE live bacteria, but with a disinfecting atmosphere of 90% relative humidity and the same exposure times gave the same result—no viable colonies at any of the four dilutions.

EXAMPLE 5

Figure 5:
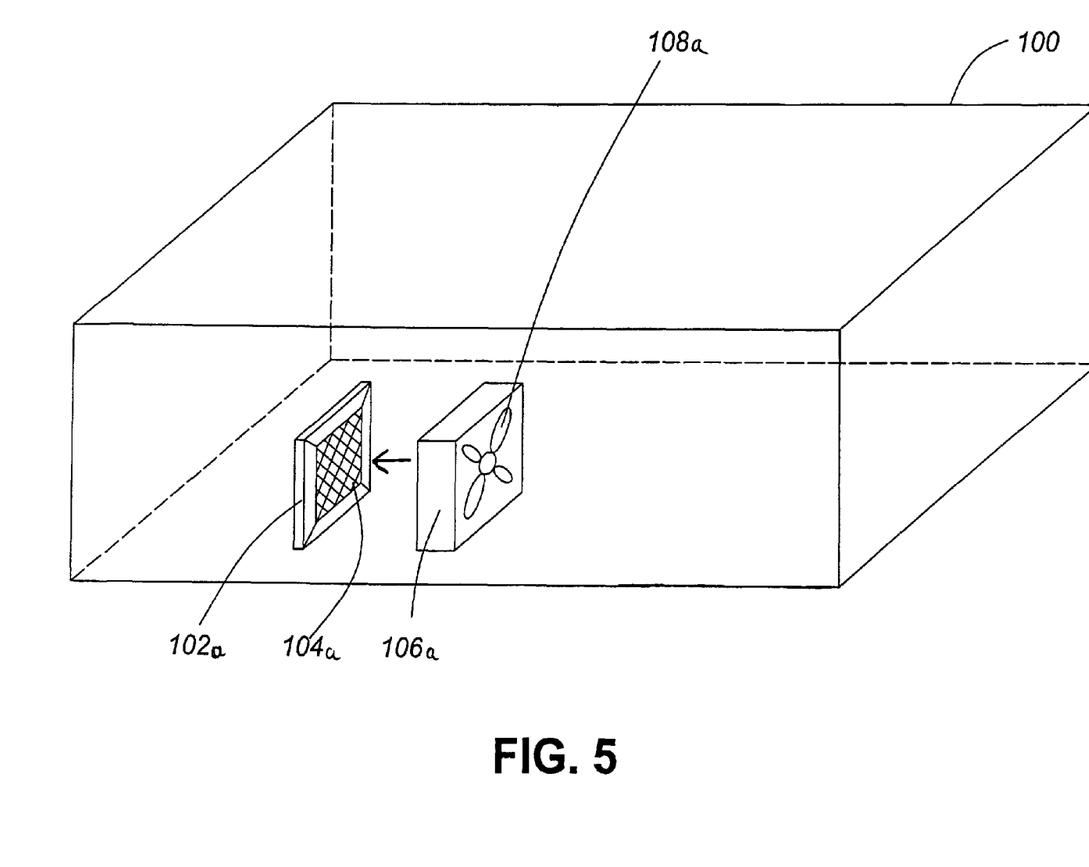
FIG. 5 is a diagrammatic illustration of a test apparatus used to disinfect soft textiles in accordance with the invention, as described in Example 5 below.

MRSA bacterially contaminated textile of the type often used as the inner layer of athletic clothing, namely gauze, was subjected to a process in accordance with an embodiment of the invention, in an apparatus diagrammatically illustrated in accompanying FIG. 5. This apparatus is essentially the same as that of FIG. 4 and used in Example 3, with the glove replaced with a frame 102a holding a layer 104a of sterile cotton gauze, impregnated with MRSA. Ozone-containing and hydrogen peroxide-containing atmosphere is fed into the chamber. An electrical fan 106a with rotary blades 108a blows the atmosphere onto the gauze with sufficient velocity to cause physical agitation of its fibrous surface. Swabbing from the gauze, selection of a single pure colony of MRSA from the swab, inoculation, incubation, serial dilution and viable colony counting took place as previously described.

Control experiments where the bacteria-carrying gauze was simply suspended in an air stream from the fan for 60 minutes but with no ozone or hydrogen peroxide supplied yielded an incubated sample where, at a 10-fold and at a 100-fold dilution, the colonies were too numerous to count. In experiments where the atmosphere comprised 1% hydrogen peroxide and 80 ppm ozone, 30 minutes exposure gave zero viable colonies at all four dilutions, for a log reduction of 8.1. An essentially identical result was obtained with a 60 minute exposure.

The experiments were repeated with gauzes carrying *P aeroginosa*, *C. difficile* and *E. coli* superbugs. No viable colonies were found at any of the four serial dilutions, in experiments using 80 ppm ozone, 1% hydrogen peroxide and humidity 80%, at 30 minutes, 45 minutes and 60 minutes exposures. The log reductions for *P aeroginosa* were 6.35 and 7.8, those for *C. difficile* were 7.9 and those for *E. coli* were 6.8.

Full results from this Example are given in the following Table.

| 1 | Organism | Ozone (PPM) | H2O2 (%) | EXP (min) | PEEP | Gauze | Direct | A | B | C | D | Log Reductions |
|---|----------|-------------|----------|-----------|------|-------|--------|------|------|-----|----|----------------|
| 2 | MRSA | 0 | 0 | 0 | 0 | Gauze | Direct | TNTC | 180 | 2 | 0 | Control |
| 3 | MRSA | 0 | 0 | 0 | 0 | Gauze | Direct | TNTC | TNTC | 181 | 12 | Control |
| 4 | MRSA | 0 | 0 | 0 | 0 | Gauze | Direct | TNTC | 223 | 21 | 3 | Control |
| 5 | MRSA | 0 | 1% | 60 | 80 | Gauze | Direct | 220 | 34 | 0 | 0 | 1.29 |
| 6 | MRSA | 0 | 1% | 90 | 80 | Gauze | Direct | 134 | 10 | 2 | 0 | 1.5 |
| 7 | MRSA | 0 | 1% | 90 | 80 | Gauze | Direct | 86 | 12 | 0 | 0 | 1.7 |
| 8 | MRSA | 0 | 1% | 60 | 80 | Gauze | Direct | 245 | 112 | 0 | 0 | 1.24 |
| 9 | MRSA | 0 | 1% | 90 | 80 | Gauze | Direct | 112 | 17 | 3 | 0 | 1.58 |
| 10 | MRSA | 0 | 1% | 90 | 80 | Gauze | Direct | 136 | 54 | 0 | 0 | 1.5 |
| 11 | MRSA | 80 | 0 | 30 | 80 | Gauze | Direct | 43 | 14 | 0 | 0 | 2 |
| 12 | MRSA | 80 | 0 | 30 | 80 | Gauze | Direct | 112 | 15 | 3 | 0 | 1.58 |
| 13 | MRSA | 80 | 1% | 30 | 0 | Gauze | Direct | 0 | 0 | 0 | 0 | 6.63 |
| 14 | MRSA | 80 | 1% | 60 | 0 | Gauze | Direct | 1 | 0 | 0 | 0 | 6.63 |
| 15 | Pseudo | 80 | 1% | 30 | 0 | Gauze | Direct | 0 | 0 | 0 | 0 | 6.35 |
| 16 | Pseudo | 80 | 1% | 60 | 0 | Gauze | Direct | 0 | 0 | 0 | 0 | 6.35 |
| 19 | C. Diff | 80 | 1% | 30 | 0 | Gauze | Direct | 0 | 0 | 0 | 0 | 7.9 |
| 20 | C. Diff | 80 | 1% | 60 | 0 | Gauze | Direct | 0 | 0 | 0 | 0 | 7.9 |
| 21 | *E. Coli* | 80 | 1% | 30 | 0 | Gauze | Direct | 0 | 0 | 0 | 0 | 6.8 |
| 22 | *E. Coli* | 80 | 1% | 60 | 0 | Gauze | Direct | 0 | 0 | 0 | 0 | 6.8 |

What is claimed is:

1. A process for treating sports equipment and sports facility rooms to inactivate superbug bacteria, consisting of: subjecting the equipment or the room, and surfaces therein, to a disinfecting atmosphere which includes ozone at an amount of 2-350 ppm by weight and hydrogen peroxide at an amount of 0.5-10 wt. %, at a relative humidity of at least 60%, wherein said amount of hydrogen peroxide is derived from a supply solution of 0.2%-10% hydrogen peroxide, and for a period of at least 30 minutes sufficient for an effective kill of the bacteria; and subsequently removing ozone from the atmosphere, down to 0.04 ppm or less.

2. The process of claim 1, wherein the ozone concentration in the disinfecting atmosphere is from 10-200 ppm.

3. The process of claim 2, wherein the ozone concentration in the disinfecting atmosphere is from 20-200 ppm.

4. The process of claim 3, wherein the ozone concentration in the disinfecting atmosphere is from 35-90 ppm.

5. The process of claim 1, wherein the hydrogen peroxide amount in the disinfecting atmosphere is from 0.5-7%.

6. The process of claim 1, wherein the hydrogen peroxide amount in the disinfecting atmosphere is from 1-5%.

7. The process of claim 1, wherein the time of exposure is from about 30 to about 120 minutes.

8. The process of claim 1, wherein the time of exposure is from about 60 minutes to about 105 minutes.

9. The process of claim 1, wherein the superbug is MRSA, VRE, *P. aeroginosa*, or *E. coli*.

10. A process for treating sports equipment and sports facility rooms to inactivate superbug bacteria, consisting of: subjecting the equipment or the room, and surfaces therein, to a disinfecting atmosphere which includes ozone at an amount of 2-350 ppm by weight and hydrogen peroxide at an amount of 0.5-10 wt. %, at a relative humidity of at least 60%, wherein said amount of hydrogen peroxide is derived from a supply solution of 0.2%-10% hydrogen peroxide, and for a period of at least 30 minutes sufficient for an effective kill of the bacteria; and subsequently removing ozone from the atmosphere, down to 0.04 ppm or less; including the additional step of subjecting fibrous or porous surfaces in the room or on the equipment to physical agitation while exposed to the disinfecting atmosphere.

11. The process of claim 10, wherein the ozone concentration in the disinfecting atmosphere is from 10-200 ppm.

12. The process of claim 11, wherein the ozone concentration in the disinfecting atmosphere is from 20-200 ppm.

13. The process of claim 12, wherein the ozone concentration in the disinfecting atmosphere is from 35-90 ppm.

14. The process of claim 10, wherein the hydrogen peroxide amount in the disinfecting atmosphere is from 0.5-7%.

15. The process of claim 10, wherein the hydrogen peroxide amount in the disinfecting atmosphere is from 1-5%.

16. The process of claim 10, wherein the time of exposure is from about 30 to about 120 minutes.

17. The process of claim 10, wherein the time of exposure is from about 60 minutes to about 105 minutes.

18. The process of claim 10, wherein the physical agitation is conducted with the application of brushes.

19. The process of claim 10, wherein the physical agitation is conducted with application of air pressure flow.

20. The process of claim 10, wherein the superbug is MRSA, VRE, *P. aeroginosa*, or *E. coli*.

* * * * *